(12) United States Patent
Inoue

(10) Patent No.: US 8,016,727 B2
(45) Date of Patent: Sep. 13, 2011

(54) STATE-OF-EXERCISE MEASURING APPARATUS AND BIOMETRIC APPARATUS

(75) Inventor: Koki Inoue, Tokyo (JP)

(73) Assignee: Tanita Corporation, Tokyo (JP)

( * ) Notice: Subject to any disclaimer, the term of this patent is extended or adjusted under 35 U.S.C. 154(b) by 191 days.

(21) Appl. No.: 12/494,863

(22) Filed: Jun. 30, 2009

(65) Prior Publication Data

US 2010/0004096 A1   Jan. 7, 2010

(30) Foreign Application Priority Data

Jul. 2, 2008   (JP) ................... 2008-172859

(51) Int. Cl.
*A63B 71/00* (2006.01)

(52) U.S. Cl. ............ 482/8; 482/1; 482/9; 482/901; 600/300

(58) Field of Classification Search ........... 482/1–9, 482/900–902; 600/300, 301, 509; 434/247
See application file for complete search history.

(56) References Cited

U.S. PATENT DOCUMENTS

| 5,469,740 | A | 11/1995 | French et al. | |
|---|---|---|---|---|
| 7,548,636 | B2 * | 6/2009 | Shimamura et al. | 382/115 |
| 2004/0167420 | A1 | 8/2004 | Song et al. | |
| 2005/0101875 | A1 * | 5/2005 | Semler et al. | 600/509 |
| 2008/0306399 | A1 * | 12/2008 | Kousaka | 600/547 |
| 2009/0182204 | A1 * | 7/2009 | Semler et al. | 600/301 |

FOREIGN PATENT DOCUMENTS

| JP | 2002-191580 | 7/2002 |
|---|---|---|
| WO | WO 02/17776 A2 | 3/2002 |
| WO | WO 2007/001219 A1 | 1/2007 |

OTHER PUBLICATIONS

European Search Report issued in European Patent Application No. 09163964.1-1265, mailed Aug. 25, 2009.

* cited by examiner

*Primary Examiner* — Glenn Richman
(74) *Attorney, Agent, or Firm* — McDermott Will & Emery LLP

(57) ABSTRACT

The invention provides a state-of-exercise measuring apparatus and a biometric apparatus configured to measure a state of exercise of a user accurately and easily in real time by calculating biometric impedances of the user doing an exercise and utilizing a change of the biometric impedances. A state-of-exercise measuring apparatus according to an aspect of the invention includes: a conducting electrode configured to come into contact with the user to supply an electric current; a measuring electrode configured to acquire a voltage of the electric current being supplied from the conducting electrode and flowing in the user's body; a biometric impedance calculating unit configured to calculate a biometric impedance of the user from a current value supplied from the conducting electrode and a voltage value measured by the measuring electrode; and a state determining unit configured to determine a state of exercise on the basis of a first biometric impedance value of the user in a predetermined state and a second biometric impedance value of the user in a state of exercise different from the predetermined state.

6 Claims, 3 Drawing Sheets

STATE-OF-EXERCISE MEASURING APPARATUS AND BIOMETRIC APPARATUS

BACKGROUND OF THE INVENTION

1. Field of the Invention

The present invention relates to a state-of-exercise measuring apparatus configured to measure a state of exercise of a user and a biometric apparatus which allows acquisition of biological data as well as the state of exercise.

2. Description of Related Art

Exercises such as muscular strength training for various objectives such as for the health maintenance and improvement (for example, fatness solution and prevention and solution of lack of exercise) or for improvement of muscular strength for various athletic events are often performed. As an example of such exercises, there is an exercise so called squat in which bending and stretching exercises of knees are repeatedly continued. The adequate speed, the magnitude or the number of times of bending and stretching movement of hand and foot are different depending on the objective or the age of exercisers, so that the exercisers are respectively needed to pay attention to do the exercises adequately. However, even though the exerciser pays an attention to do the exercises adequately, there are cases where the speed of movement is reduced or the magnitude of the bending and stretching movement of hand and foot is reduced after the repetition of the exercise, for example, due to fatigue. In contrast, there is a case where the speed or the number of times of the exercises is increased more than necessary with strain. Therefore, means for supporting the exercise adequate for the exerciser objectively is necessary, and adequate measurement of kinetic energy consumed by the exercise (consumed calories) is also required.

As such means, by using a triaxial acceleration sensor as used in various body movement detecting apparatuses proposed in recent years (for example, JP-A-2002-191580), the number of times of the repetitive and continuous exercises may be counted and, in addition, by combining the counted value and biological data such as the age or the weight, the energy consumed by the exercise may be calculated according to the counted value.

However, when an acceleration sensor is used, the number of times of the exercises as described above is counted, but whether the exercises are done repeatedly at a certain ideal speed or not, or whether the magnitude of the bending and stretching exercises is sufficiently large or not cannot be detected. Although the acceleration sensor detects whether the body movement is occurred or not, it cannot detect whether the posture standing on one leg in an exercise to maintain the posture standing on one leg is maintained or not, or whether a predetermined body weight shift is done in the exercise to shift the body weight (center of gravity).

As other means, doing the exercise while confirming a video shot by a video camera on a monitor or the like is considered. However, the apparatus is upsized, and inconveniences such as cost increase or troublesome setting cannot be avoided.

SUMMARY OF THE INVENTION

In view of such circumstances, it is an object of the invention to provide state-of-exercise measuring apparatus and a biometric apparatus configured to measure a state of exercise of a user accurately and easily in real time by calculating biometric impedances of the user doing an exercise and utilizing a change of the biometric impedances.

In order to solve the above-described problems, a state-of-exercise measuring apparatus according to a first aspect of the invention includes: a conducting electrode configured to come into contact with a user to supply an electric current; a measuring electrode configured to acquire a voltage of the electric current being supplied from the conducting electrode and flowing in the user's body; a biometric impedance calculating unit configured to calculate a biometric impedance of the user from a current value supplied from the conducting electrode and a voltage value measured by the measuring electrode; and a state determining unit configured to determine a state of exercise on the basis of a first biometric impedance value of the user in a predetermined state and a second biometric impedance value of the user in the state of exercise different from the predetermined state.

Preferably, the state-of-exercise measuring apparatus includes an exercise setting unit configured to set conditions of exercise including the state of exercise, and the state determining unit determines whether the state of exercise satisfies the conditions of exercise or not by comparing the calculated biometric impedance of the user with the first biometric impedance value and the second biometric impedance value.

Preferably, the state-of-exercise measuring apparatus includes a notifying device configured to notify the user that the conditions of exercise are satisfied and/or the conditions of exercise are not satisfied.

Preferably, the state-of-exercise measuring apparatus includes a kinetic energy calculating unit configured to calculate kinetic energy that the user consumes and a display unit configured to display a result of calculation by the kinetic energy calculating unit.

Preferably, the state of exercise includes at least one of being in a state in which knees are bent, being in a state in which arms are bent, and being in a state of standing on one leg.

Preferably, the state-of-exercise measuring apparatus includes a plurality of weight sensing units configured to sense the weight of the user riding on the state-of-exercise measuring apparatus and a balance determining unit configured to determine the body weight shift of the user by comparing respective results sensed by the respective weight sensing units.

A biometric apparatus according to a second aspect of the invention includes a state-of-exercise measuring apparatus according to the first aspect of the invention, a biological data setting unit configured to set first biological data of the user, and a calculating unit configured to calculate second biological data on the basis of the first biometric impedance value or the second impedance value and the first biological data.

According to the state-of-exercise measuring apparatus and the biometric apparatus of the invention, the user is able to grasp his or her own state of exercise in real time accurately and easily.

DESCRIPTION OF PREFERRED EMBODIMENT

Figure 1:
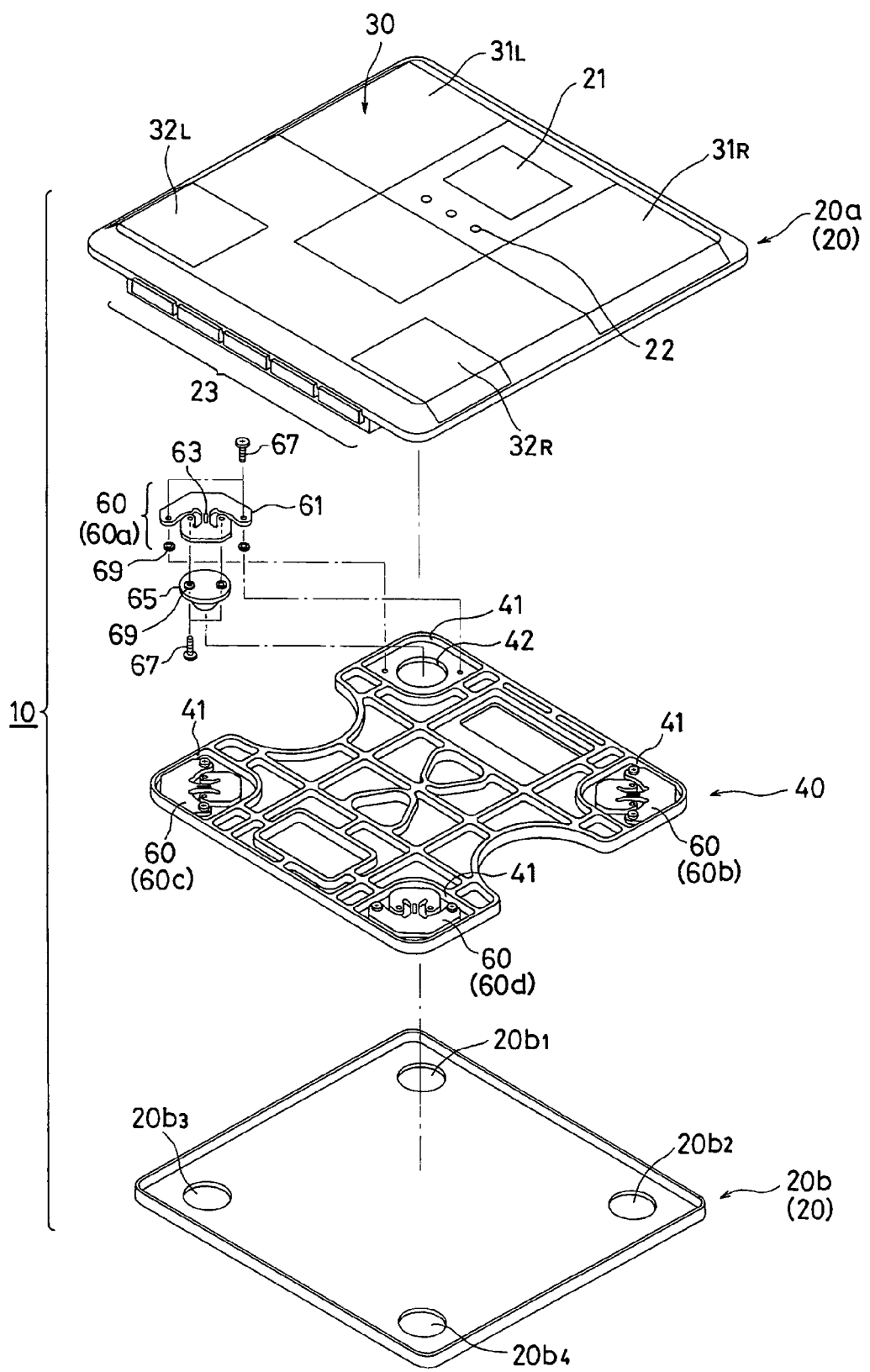
FIG. 1 is an exploded perspective view showing a configuration of a biometric apparatus according to an embodiment of the invention.

Referring now to the drawings, the invention will be described in detail on the basis of an embodiment in a case where the invention is applied to a biometric apparatus (state-of-exercise measuring apparatus) which achieves not only a measurement of a state of exercise performed by acquiring biometric impedances of a user but also a measurement of the weight and the percentage of body fat of the user. The apparatus according to the embodiment of the invention may include only a function to acquire the biometric impedances of the user and measure the state of exercise of the user using the same, or, alternatively, a configuration in which the function of weight measurement or a function to calculate the biological data such as the percentage of body fat is eliminated from the biometric apparatus describe below is also applicable.

Figure 2:
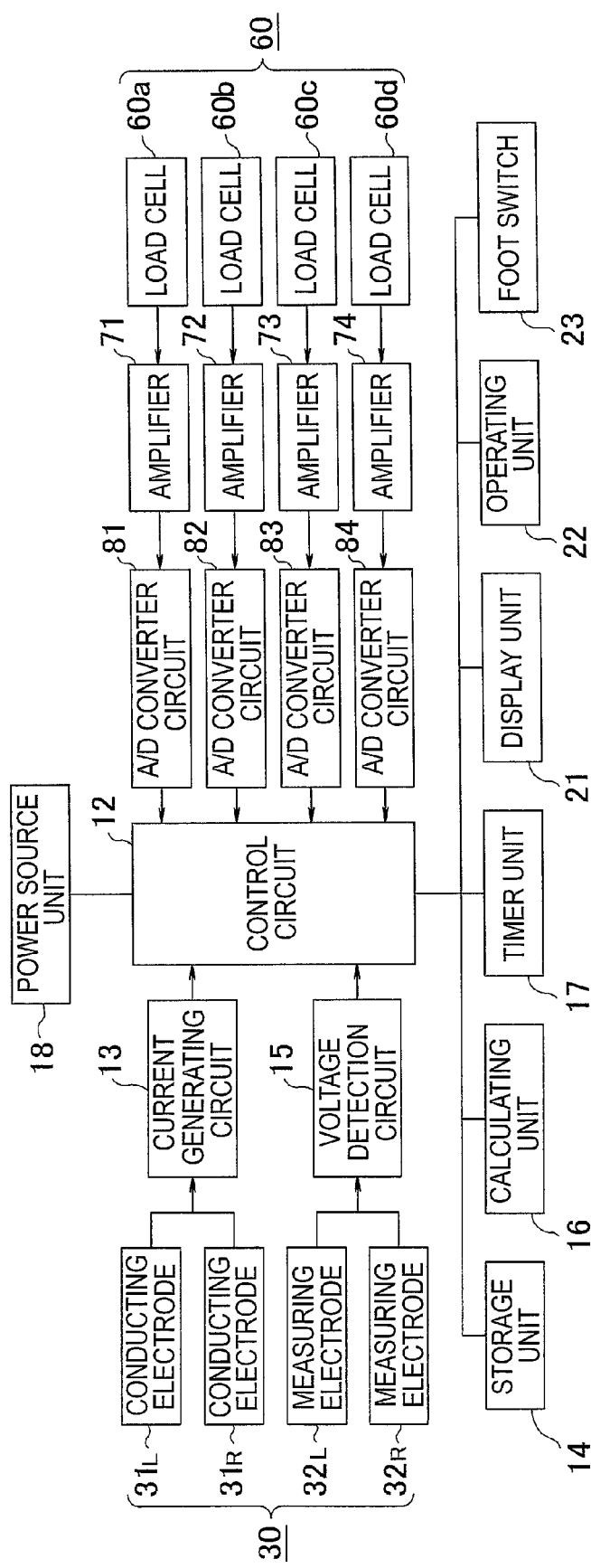
FIG. 2 is a block diagram showing a control system relating to a weight measurement and a biological data acquisition of the biometric apparatus according to the embodiment of the invention.

FIG. 1 is an exploded perspective view showing a configuration of a biometric apparatus 10 according to the embodiment, and FIG. 2 is a block diagram showing a control system of the biometric apparatus 10.

As shown in FIG. 1, the biometric apparatus 10 includes a machine body 20 formed substantially into a box shape, and leg portions 65 provided so as to project from a back side of the machine body 20 (the back side of a bottom plate member 20b) for supporting the machine body 20. As shown in FIG. 1 or FIG. 2, the machine body 20 includes a display unit 21, an operating unit 22, a foot switch 23, an electrode member 30, a frame member 40, a control circuit 12, a current generating circuit 13, a voltage detection circuit 15, a storage unit 14, a calculating unit 16, a timer unit 17, a power source unit 18, load cells 60, amplifiers 71, 72, 73, and 74 as amplifying circuits, and A/D converter circuits 81, 82, 83, and 84. Detailed configurations of the respective members will be described below.

The machine body 20 is formed substantially into a flat box shape by combining a cover member 20a formed by molding a resin (for example, ABS resin (acrylonitrile/butadiene/styrene copolymer), glass) or the like and the bottom plate member 20b formed of metal.

As shown in FIG. 1, thin-plate shaped four electrode members 30 (conducting electrodes $31_L$ and $31_R$ and measuring electrodes $32_L$ and $32_R$) are held on an upper surface of the cover member 20a of the machine body 20, and these members are arranged apart from each other on the upper surface of the cover member 20a. As described later, the conducting electrodes $31_L$ and $31_R$ are electrically connected to the current generating circuit 13, and the measuring electrodes $32_L$ and $32_R$ are also electrically connected to a voltage detection circuit 415 respectively.

In the embodiment, the electrode member 30 includes four in total of the conducting electrodes $31_L$ and $31_R$ and the measuring electrodes $32_L$ and $32_R$. However, the number of the electrodes is not limited to four. For example, the electrode member 30 may include two electrodes which have functions of both the conducting electrode and the measuring electrode. In contrast, it is also possible to provide, in addition to the electrode member 30, another electrode member (hand electrode) in a grip member electrically connected to the machine body 20 with a connecting cord and allows the user to grip with both hands.

As shown in FIG. 2, the display unit 21, the operating unit 22, the foot switch 23, the storage unit 14, the calculating unit 16, the timer unit 17, and the power source unit 18 are connected to the control circuit 12.

The display unit 21 is a data display device (display device) configured to display data sent from the control circuit 12 and displays mainly a state of exercise or conditions of exercise (the duration of the exercise, the number of times of exercise, notification to notify whether the conditions of exercise are satisfied or not) of the user, described later, as well as various biological data of the user or an operating method. For example, a display unit employing liquid crystal such as a full-dot LCD (Liquid Crystal Display) may be used as the display unit 21, and the display unit 21 and the operating unit 22 may be formed integrally as a liquid crystal display panel having, for example, a touch-panel function.

The operating unit 22 is a data input device (input device) for allowing the user to input his or her biological data (for example, sex, age, and height), to set various setting items of the biometric apparatus 10 (for example, the size of characters or signs displayed on the display unit 21), and to set the conditions of exercise, described later. In the embodiment, the operating unit 22 is of a three-button system provided on the near side of the display unit 21 of the machine body 20 as an example, the number, the shape, the method of operation, and the position of arrangement are not limited thereto and, for example, a touch sensor system or a dialing system may also be selected as needed. The foot switch 23 also functions as an input device, and is configured to function as a user-specific register key in a case where a plurality of users utilize the same biometric apparatus 10 or to allow turning ON and OFF the biometric apparatus 10. When the operating unit 22 or the foot switch 23 is operated by the user, corresponding signals are outputted to the control circuit 12. The biological data and the setting items of the user entered with such operations are stored in the storage unit 14 or displayed on the display unit 21. Also, it is configured to allow the data to be read out from the storage unit 14 and displayed on the display unit 21, to select one of exercise measuring modes stored in the storage unit 14 in advance, or to display the result of measurement in sequence.

The timer unit 17 is configured to measure a lapse of a predetermined time, or determined whether the predetermined time is elapsed or not. In the embodiment, the timer unit 17 is an independent component. However, it may be integrated into the control circuit 12 as a timer circuit to determine whether the predetermined time is elapsed or not by the control circuit 12 itself.

As the power source unit 18, batteries for supplying an electric power to operate the biometric apparatus 10 or an external power source may be utilized.

The storage unit 14 is a storage device configured with a ROM (non-volatile memory (Read Only Memory), a RAM (volatile memory (Random Access Memory)) and stores various data. The data includes, for example, various data or programs used in processes in the control circuit 12 and acquired user-specific biological data. Reading and writing of the data as described above are performed by the control circuit 12.

The control circuit 12 and the calculating unit 16 are each formed of an integrated circuit. In addition, although the control circuit 12 and the calculating unit 16 may be formed of separate integrated circuits, a common integrated circuit is also applicable.

The load cells 60 (60a, 60b, 60c, and 60d) as weight sensing units are connected to the control circuit 12 via the A/D converter circuits 81, 82, 83, and 84 and the amplifiers 71, 72, 73, and 74 as the amplifying circuits.

The weight sensing unit is configured to measure a load (weight) of the user riding on the machine body 20 and, as shown in FIG. 1 or FIG. 2, the load cells 60 include a flexure element 61 formed of a metallic member which deforms according to a load being applied and a strain gauge 63 bonded to the flexure element 61. The strain gauge 63 constitutes part of Wheatstone bridge, and is configured to grasp a deflection (expansion and contraction) of the flexure element 61 due to the weight of the user as a change in value of electric resistance.

The load cells 60 are attached to the machine body 20 as follows as an example. The substantially plate shaped frame member 40 is provided between the cover member 20a and the bottom plate member 20b, which constitute the machine body 20, so as to come into abutment with a back surface side of the cover member 20a. The frame member 40 is formed of a material having a high strength such as metal (aluminum or the like), and mounting recesses 41 which allow the load cells 60 (60a, 60b, 60c, and 60d) to be stored and mounted one by one are formed at four corners of the upper surface (the surface on the side of the cover member 20a), and circular holes 42 which allow insertion of the leg portions 65 are formed in the respective mounting recesses 41. On the other hand, the bottom plate member 20b is formed with holes $20b_1$, $20b_2$, $20b_3$, and $20b_4$ which allow the insertion of the leg portions 65 are provided at positions corresponding to the circular holes 42.

The leg portion 65 is secured to one end of the respective load cells 60 (60a, 60b, 60c, and 60d) with a screw 67 with the intermediary of a spacer 69, and the other end of the respective load cells 60 is secured to the respective mounting recesses 41 with the screw 67 with the intermediary of the spacer 69. In FIG. 1, a state before mounting the load cell 60a and after mounting the load cells 60b, 60c, and 60d is shown.

When the frame member 40 on which the respective load cells 60 are mounted in the respective mounting recesses 41 is provided between the cover member 20a and the bottom plate member 20b which constitute the machine body 20, the leg portions 65 attached to the respective load cells 60 protrude from the respective holes $20b_1$, $20b_2$, $20b_3$, and $20b_4$ of the bottom plate member 20b, the biometric apparatus 10 comes into contact with the ground with the leg portions 65.

Accordingly, when the flexure element 61 is deflected by the load applied when the user rides on the upper surface of the machine body 20, the strain gauge 63 is expanded and contracted, so that the output value according to the expansion and contraction of the strain gauge 63 changes, and the change is read as the change of the output of the load signal, whereby the weight is measured. In other words, the calculating unit 16 obtains the weight from the difference between output values from the load cells 60 when no load is applied to the machine body 20 (so-called zero point) and output values when the load is applied thereto, so that the weight of the user is measured. The weight of the user measured in this manner is stored in the storage unit 14, and is displayed on the display unit 21.

The conducting electrodes $31_L$ and $31_R$ and the measuring electrodes $32_L$ and $32_R$ are connected respectively to the control circuit 12 via the current generating circuit 13 and the voltage detection circuit 15.

In the embodiment, the two electrode members $31_L$ and $31_R$ on the display unit 21 side from among the four electrode members 30 are conducting electrodes and the electrode members $32_L$ and $32_R$ on the other side are measuring electrodes. The current generating circuit 13 is connected to the conducting electrodes $31_L$ and $31_R$, and a predetermined fine electric current is supplied thereto according to a command signal from the control circuit 12. On the other hand, the voltage detection circuit 15 is connected to the measuring electrodes $32_L$ and $32_R$, and the voltage between the measuring electrodes is measured. In this manner, the electric current is fed to the user's body from the conducting electrodes, and the voltage generated in a current path is measured by the measuring electrodes.

As measurable voltages here, in order to allow accurate measurement of various types of state of exercise assumed by the user, for example, the following measurement is exemplified. (1) For example, when doing the bending and stretching exercise of the knees such as the squat, the voltage between the measuring electrodes $32_L$ and $32_R$ which are in contact with the respective foot is measured in the current path flowing from one foot side of the user (for example, the conducting electrode $31_R$) to the other foot side (for example, the conducting electrode $31_L$) via the legs and underbelly in a state in which the user stands on both legs on the machine body 20. Also, when accurate measurement of the percentage of body fat is wanted as well in addition to the case of measuring the state of exercise, it is achieved by the measurement of the voltage in the same manner. Also, (2) For example, when doing an exercise such as a push-up, the voltage between the measuring electrodes $32_L$ and $32_R$ which are in contact with the respective hand is measured in the current path flowing from one hand side of the user (for example, the conducting electrode $31_R$) to the other hand side (for example, the conducting electrode $31_L$) via the arms and chest in a state in which the user places his or her hands under himself or herself on the machine body 20 with the legs placed out of the machine body 20. (3) When doing the exercise such as maintaining the posture standing on one leg, the electric current does not flow from the one conducting electrode (for example, the conducting electrode $31_L$) to the other conducting electrode (the conducting electrode $31_R$) in the state in which the user stands on one leg on the machine body 20, there is no voltage drop when the voltage between the measuring electrodes $32_L$ and $32_R$ is measured, so that it is determined that the user stands on one leg.

As in this embodiment, it is not necessary to fix the function by determining the electrode members $31_L$ and $31_R$ as the conducting electrodes and the electrode members $32_L$ and $32_R$ as the measuring electrodes. A configuration in which the connection between the electrode member 30 and the current generating circuit 13 or the voltage detection circuit 15 is adapted to be switchable so as to allow all the electrode members 30 to be selectively changed the functions as the conducting electrode and as the measuring electrode, or a configuration in which the electrode members 30 is connected to the current generating circuit 13 and the voltage detection circuit 15 so as to allow the respective electrode members 30 to achieve both functions as the conducting electrode and the measuring electrode. In this configuration (4) For example, measurement of the voltage is also achieved when the bending and stretching movement of the knee in the posture standing on one leg.

In other words, in the current path flowing from the grounded foot (for example, the electrode member $31_L$ as the conducting electrode) to the same foot (for example, the electrode member $32_L$ as the conducting electrode) via the leg portion of the grounded foot or the like, the voltage between the electrode members $31_L$ and $32_L$ as the measuring electrode which is in contact with the corresponding foot may be measured, and since there is no voltage drop between the pair of electrode members (for example, the electrode members $31_R$ and $32_R$) which are not in contact with the foot, determination of which one of the left and right legs the user is standing on is enabled.

Under the control of the control circuit 12, the calculating unit 16 is able to obtain the biometric impedances of the user on the basis of the supplied current value and the measured voltage value as described above, and the calculating unit 16 in this case functions as the biometric impedance calculating unit. The biometric impedances of the user obtained in this manner is outputted and stored in the storage unit 14.

Here, the biometric impedances change depending on the current path in the user's body in which the electric current flows from the one conducting electrode to the other conducting electrode, so that the measuring electrode reads different voltages. For example, the current path flowing from the one foot side of the user to the other foot side via the legs and underbelly in a state in which the user stands on both legs on the machine body 20 is different between a state in which the user assumes an erect posture and a posture with bent knees, so that the biometric impedances in the respective states are also different and the different voltages are measured. Also, when the knees are bent gradually deeper, the biometric impedance is gradually reduced, so that the measured voltage varies correspondingly. In the same manner, the current path flowing from one hand side of the user to the other hand side via the arms and chest is different between a state in which the user stretches the arms and a state in which the user bends the arms, so that the biometric impedances in the respective states are different, and the different voltages are measured. Also, when the arms are bent gradually deeper, the biometric impedance is gradually reduced, so that the measured voltage varies correspondingly gradually.

Therefore, by setting the biometric impedances in the state of the erect posture and the state in which the knees or the arms are bent by a predetermined angle as threshold values according to the height, the sex, or the like of the user, and comparing the biometric impedances as the threshold values and the biometric impedances measured in real time when doing the exercise to bend and stretch the knees or the arms actually, total determination such as whether or not the knees or the arms bent to an extent exceeding the predetermined angle, how much they are bent, how fast (pitches) they are bent and stretched, and how many number of times they are bent and stretched is achieved. Such a comparison and determination process is performed by the calculating unit 16 as the state determining unit under the control of the control circuit 12.

The state determination as described above is performed after having set the conditions of exercise including the state of exercise before starting the exercise in advance. The state of exercise here means the type of the exercise that the user does, and includes the bending and stretching movement of the knees such as the squat, the bending and stretching movement of the arms such as the push-up, and the exercise to maintain the predetermined posture such as the standing on one leg for a certain period of time. The conditions of exercise mean conditions including the type of the exercise and the duration of the exercise, for example, include the objective of the exercise (for example, fatness solution and prevention, solution of lack of exercise, and improvement of muscular strength), the depth of the bending and stretching exercise, the duration, the speed (pitches), and the number of times. The conditions of exercise are stored at least partly in the storage unit 14 in advance, and are adapted to be displayed on the display unit 21 so that the user is able to select before starting the exercise, for example. The user operates the operating unit 22 and selects the exercise to be done from the displayed conditions of exercise. Accordingly, the conditions of exercise corresponding to the selected exercise are read from the storage unit 14, and are supplied to the state determination. The conditions of exercise may be selected or set further in detail using the operating unit 22. As regards the setting of the conditions of exercise, it is preferable that the effective conditions for achieving the objective of the exercise are programmed to be set automatically on the basis of the biological data such as the age, height, weight, and sex of the user.

The calculating unit 16 is a state determining unit configured to compare the state of exercise of the user and the preset condition of exercise and determine whether the conditions of exercise are satisfied or not, and the results are stored in the storage unit 14. The calculating unit 16 is able to calculate calories that the user consumes on the basis of the selected conditions of exercise, and data indicating whether the exercise has been done with the conditions of exercise satisfied or not, and the results are stored in the storage unit 14.

Although the control circuit 12, the current generating circuit 13, the storage unit 14, the voltage detection circuit 15, the calculating unit 16, the timer unit 17, the power source unit 18, the amplifiers 71, 72, 73, and 74, and the A/D converter circuits 81, 82, 83, and 84 as described above are not shown in the drawings other than FIG. 2, they may be arranged at given positions of the biometric apparatus 10, for example, on a lower surface of the cover member 20a or on the frame member 40 as needed.

The control circuit 12 and the calculating unit 16 calculate the weight or the biometric impedances after having converted the voltage value or the output value acquired by the voltage detection circuit 15 and the load cells 60 from analogue values to digital values as described above, and calculates the biological data such as the percentage of body fat by applying parameters such as the entered biological data (height, sex, and age, etc.), the weight and the biometric impedances to a regression formula determined in advance. The types of the biological data obtained by such calculation may be selected as needed depending on the objective of usage of the biometric apparatus according to the invention, and exemplified by the percentage of body fat, offal fat level (offal fat surface area), body water content, muscle mass, basal metabolism rate, bone mass, lean body mass, body cell mass, blood pressure, BMI (Body Mass Index), degree of obesity, intracellular fluid volume, and extracellular fluid volume. The biological data acquired in the manner described above are stored in the storage unit 14.

Furthermore, by comparing the distortions sensed by the respective load cells 60 (60a, 60b, 60c, and 60d) respectively, the direction in which the user riding on the machine body 20 applies his or her weight may be determined. In this determining process, the calculating process for comparing the distortions in the respective load cells 60 is performed in the calculating unit 16 (balance determining unit) under the control of the control unit 12. By using this calculating process, determination of the state of exercise of the user when doing the exercise in which the balance of the body is changed on the machine body 20 including the action to stand on one leg is achieved.

Figure 3:
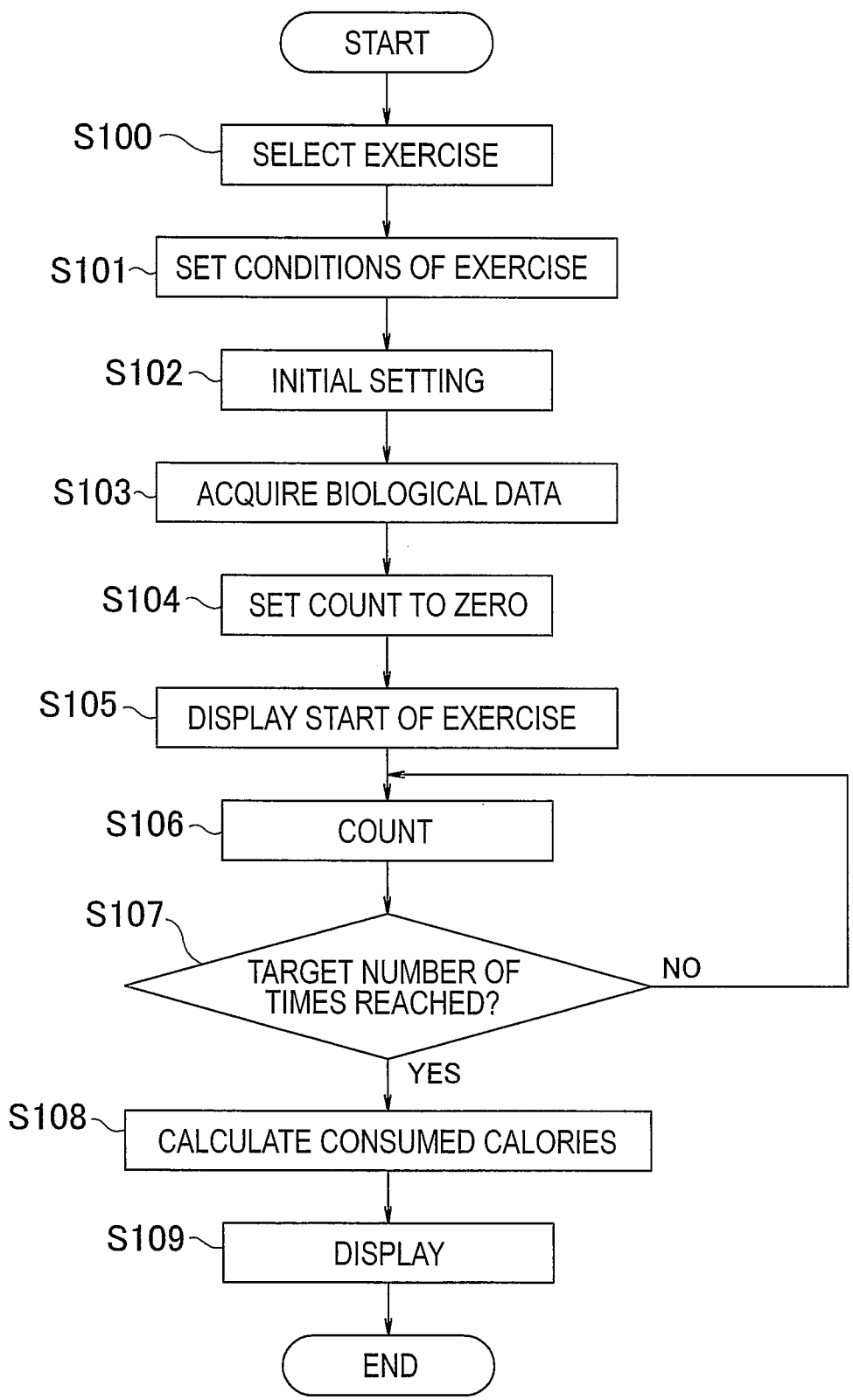
FIG. 3 is a flowchart showing a flow of determination of a state of exercise and acquisition of the biological data using the biometric apparatus according to the embodiment of the invention.

Referring now to FIG. 3, an example of a flow of determination of the state of exercise and acquisition of the biological data in the biometric apparatus 10 will be descried. FIG. 3 is a flowchart showing a flow of determination of the state of exercise and acquisition of the biological data using the biometric apparatus 10.

FIG. 3 shows a case of doing the bending and stretching movement (squat) as an example of the state of exercise and shows a flow until the bending and stretching movements are done by the number of times set in an initial setting and are ended.

When the foot switch 23 or the like is operated, after having passed the steps of activation of the biometric apparatus 10 and reading out of personal data, the exercise measuring mode is started. Then, a list of determinable exercises is displayed on the display unit 21. The user selects the bending and stretching movement of the knee from the list with the operating unit 22 (Step S100).

When the exercise is selected, an input guide screen for entering the conditions of exercise is displayed on the display unit 21. The user sets conditions of exercise of the bending and stretching movement of the knees using the operating unit 22 (exercise setting unit) (Step S101). In an example shown in FIG. 3, the number of times of the bending and stretching exercises (the number to be counted) is set. The set conditions of exercise are stored in the storage unit 14. Conditions other than the number of times can also be set as a matter of course in the invention. For example, the speed of the exercise (pitches) may be set simultaneously in addition to the number of times described above.

Subsequently, as an initial setting, a biometric impedance value in a state before doing the exercise (in a predetermined state, that is, in a state in which the knees are stretched in the bending and stretching exercise of the knees in FIG. 3) (first biometric impedance value) and a biometric impedance value (second biometric impedance value) in the state of exercise (a state in which the knees are bent in the bending and stretching movement of the knee in FIG. 3) are acquired (Step S102).

As regards the predetermined conditions, the biometric impedances of the user are obtained on the basis of a voltage measured between the measuring electrodes $32_L$ and $32_R$ by supplying the electric current from the conducting electrodes $31_L$ and $31_R$ in a state in which the user assumes the erect posture on the machine body 20 with his or her left foot in contact with the conducting electrode $31_L$ and the measuring electrode $32_L$ and his or her right foot in contact with the conducting electrode $31_R$ and the measuring electrode $32_R$ respectively. The user sets the obtained biometric impedance value as the biometric impedance value in the state before doing the exercise and stores the same in the storage unit 14 using the operating unit 22.

As the state of exercise, the user bents his or her knees to a position which is set by the user as a state of bending the knees to a sufficiently deep position as the bending and stretching movement and rest there, and then the biometric impedance is obtained again. The user sets the obtained biometric impedance value as the biometric impedance value (second biometric impedance value) in the state of exercise and stores the same in the storage unit 14 using the operating unit 22.

The predetermined state does not necessarily mean the erect state, and may be set to a given state according to the type of the exercise. For example, in the case of the bending and stretching movement of the knees shown in FIG. 3, the state of bending the knees to a deepest position may be set as the predetermined state instead of the erect posture.

Subsequently, acquisition of the biological data is performed (Step S103). As regards the weight, the deformations of the flexure elements 61 in the respective load cells 60 (60a, 60b, 60c, and 60d) are outputted by the strain gauges 63 as the change in values of electric resistance, and are amplified by the amplifiers 71, 72, 73, and 74 respectively, and then are converted into digital signals by the A/D converter circuits 81, 82, 83, and 84 respectively, so that the weight of the user is calculated according to the program stored in the storage unit 14 in advance. Since the biological data other than the weight such as the percentage of body fat does not specifically have to be acquired in this exercise measuring mode, the acquisition process thereof does not have to be performed.

Subsequently, the control circuit 12 sets the counted number of the number of times of exercise to zero (Step S104) and then causes the display unit 21 to display a screen indicating that the exercise can be started (Step S105). The user starts exercise after having confirmed this screen.

The biometric apparatus 10 measures the biometric impedances of the user continuously after having displayed the start of exercise. The biometric impedance values acquired continuously are stored in the storage unit 14 in correspondence with the measured timings acquired from the timer unit 17.

When the continuously acquired biometric impedance values reach the biometric impedance value in the state of exercise which is already set in the initial setting (second biometric impedance value) and then are returned back to the biometric impedance value before starting the exercise which is already set in the initial setting (first biometric impedance value), it is determined that the knees are bent once to the predetermined depth and the counted number is incremented by one (Step S106). In contrast, when the continuously acquired biometric impedance values do not reach the biometric impedance value in the state of exercise, or when they reach once and do not return to the biometric impedance value before doing the exercise, it is determined that the knees are not bent to the predetermined depth and hence the counted number is not incremented.

By the provision of a notifying device which notifies the user whether the state of exercise satisfies the conditions of exercise or not such as the case in which the counted number is incremented and the case in which the counted number is not incremented, the motivation of exercise is enhanced or the state is preferably grasped in real time during the exercise. As the notifying device, for example, a speaker unit (not shown) which outputs a sound effect or a voice announcement or a light-emitting unit (not shown) which outputs light may be provided, or display on the display unit 21 is also contemplated.

After having started the exercise, the control circuit 12 determines whether the counted number reaches a target number of times determined in the setting of the conditions of exercise or not (Step S107). When the target number of times is not reached (No in Step S107), the counted number is repeatedly observed.

In contrast, when the counted number reaches the target number of times (YES in Step S107), the fact that the conditions of exercise are satisfied, and the target number of times are reached is displayed on the display unit 21. At this time, the control circuit 12 causes the calculating unit 16 (kinetic energy calculating unit) to calculate the kinetic energy (consumed calories) consumed by the user on the basis of the weight value or the total counted number (Step S108). Here, the kinetic energy (consumed calories) is calculated according to the type of exercise and the number of times of doing the exercise. A calculation program is stored in the storage unit 14 in advance. Furthermore, the control circuit 12 causes the display unit 21 to display the weight value and the calculated kinetic energy (consumed calories) (Step S109).

In FIG. 3, the bending and stretching movement is exemplified. However, the biometric apparatus 10 may be used for the measurement of exercises other than the bending and stretching movement of the knee such as the push-up as the bending and stretching movement of the arms, balance exercise, and leg lift exercise. The user is able to grasp the state of exercise in these exercises accurately in real time.

For example, the exercise such as the push-up may be done by bending and stretching the user's arms in a state in which the hands are placed under the body on the machine body 20 so as to come into contact with the electrode members 30 and the legs are placed out of the machine body 20, and other detailed processes are the same as the bending and stretching movement of the knees described above.

In the case of the balance exercise in which the weight is shifted with the feet kept in contact with the conducting electrodes $31_L$ and $31_R$ and the measuring electrodes $32_L$ and $32_R$, the biometric impedances are acquired while observing the fact that the conducting electrodes $31_L$ and $31_R$ and the measuring electrodes $32_L$ and $32_R$ are in continuity with each other, and the control circuit 12 compares the output values from the respective load cells 60 with respect to each other, so that the balance of the user on the machine body 20 is determined depending on the magnitude of the output values. In the case of the balance exercise, for example, the erect posture is set as the predetermined state, and the distribution of the output values from the load cells 60a, 60b, 60c, and 60d when the body is slanted to the maximum may be set as the state of exercise.

In contrast, in the case of the exercise in which the foot is moved apart from part of the electrode members 30 temporarily or continuously as the leg lift exercise, for example, the erected state with the feet placed on the conducting electrodes $31_L$ and $31_R$ and the measuring electrodes $32_L$ and $32_R$ is set as the predetermined state, and the state of exercise may be set arbitrarily according to the contents of the exercise. Also, by observing the fact that the pair of electrodes is in continuity with each other using the conducting electrodes $31_L$ and $31_R$ and the measuring electrodes $32_L$ and $32_R$, which leg is lifted can be determined. Alternatively, determination of the fact that at least one of the legs is lifted may be made on the basis of the fact that there is not voltage drop between the measuring electrodes because the pair of conducting electrodes is not in continuity, so that the biometric impedance is not calculated.

In the above-described configuration, the following advantages are achieved according to the embodiment described above.

(1) Since the state of exercise is grasped while doing the exercise on the state-of-exercise measuring apparatus, the accurate observation of the state of exercise is achieved in real time.

(2) Setting before the measurement may be done by the user easily.

(3) Since part of the functions of the biometric apparatus in the related art may be utilized, an inexpensive and compact apparatus is achieved.

(4) By storing the state of exercise in the storage unit 14, comparison with the states of exercise in other opportunities is also achieved.

(5) Since the acquisition of the biological data together with the measurement of the state of exercise is possible, the effect of the exercise is known immediately.

Although the invention has been described on the basis of the above-described embodiment, the invention is not limited to the above-described embodiment, and may be improved or modified within the scope of the object of the improvement and the spirit of the invention. For example, although the state-of-exercise measuring apparatus and the biometric apparatus used mainly by placing on the floor have been described in the embodiment shown above, a configuration in which the user uses in a state of holding and lifting with both hands or one hand and the bending and stretching movement of the arms is measured in this state is also applicable. Although the configuration in which the four load cells 60 as the weight sensing devices are arranged at the four corners of the machine body 20 has been described in the embodiment shown above, a configuration in which the load cells are arranged in the front, rear, left, and right of the machine body 20 and eight in total of the load cells are provided for enabling further accurate determination of the weight balance is also applicable.

What is claimed is:

1. A state-of-exercise measuring apparatus comprising:
a conducting electrode configured to come into contact with a user to supply an electric current;
a measuring electrode configured to acquire a voltage generated in a current path of the electric current being supplied from the conducting electrode and flowing in the user's body;
a biometric impedance calculating unit configured to calculate a biometric impedance of the user from a current value supplied from the conducting electrode and a voltage value measured by the measuring electrode;
an exercise setting unit configured to set conditions of exercise including the state of exercise;
a storage unit configured to store a first biometric impedance value of the user in a predetermined state and a second biometric impedance value of the user in a state of exercise different from the predetermined state; and
a state determining unit configured to determine whether the state of exercise satisfies the conditions of exercise or not by comparing the calculated biometric impedance of the user with the first biometric impedance value and the second biometric impedance value.

2. The state-of-exercise measuring apparatus according to claim 1, further comprising:
a notifying device configured to notify the user that the conditions of exercise are satisfied and/or the conditions of exercise are not satisfied.

3. The state-of-exercise measuring apparatus according to claim 1, further comprising:
a kinetic energy calculating unit configured to calculate kinetic energy that the user consumes and a display unit configured to display a result of calculation by the kinetic energy calculating unit.

4. A state-of-exercise measuring apparatus comprising:
a conducting electrode configured to come into contact with a user to supply an electric current;
a measuring electrode configured to acquire a voltage generated in a current path of the electric current being supplied from the conducting electrode and flowing in the user's body;
a biometric impedance calculating unit configured to calculate a biometric impedance of the user from a current value supplied from the conducting electrode and a voltage value measured by the measuring electrode; and
a state determining unit configured to determine a state of exercise on the basis of a first biometric impedance value of the user in a predetermined state and a second biometric impedance value of the user in a state of exercise different from the predetermined state,
wherein the state of exercise includes at least one of being in a state in which knees are bent, being in a state in which arms are bent, and being in a state of standing on one leg.

5. A state-of-exercise measuring apparatus comprising:
a conducting electrode configured to come into contact with a user to supply an electric current;
a measuring electrode configured to acquire a voltage generated in a current path of the electric current being supplied from the conducting electrode and flowing in the user's body;
a biometric impedance calculating unit configured to calculate a biometric impedance of the user from a current value supplied from the conducting electrode and a voltage value measured by the measuring electrode;

a state determining unit configured to determine a state of exercise on the basis of a first biometric impedance value of the user in a predetermined state and a second biometric impedance value of the user in a state of exercise different from the predetermined state;

a plurality of weight sensing units configured to sense the weight of the user riding on the state-of-exercise measuring apparatus; and a balance determining unit configured to determine a body weight shift of the user by comparing respective results sensed by the weight sensing units.

6. A biometric apparatus comprising:

a state-of-exercise measuring apparatus;

a biological data setting unit configured to set first biological data of the user; and a calculating unit configured to calculate second biological data on the basis of the first biometric impedance value or the second biometric impedance value and the first biological data, wherein the state-of-exercise measuring apparatus comprises:

a conducting electrode configured to come into contact with a user to supply an electric current;

a measuring electrode configured to acquire a voltage generated in a current path of the electric current being supplied from the conducting electrode and flowing in the user's body;

a biometric impedance calculating unit configured to calculate a biometric impedance of the user from a current value supplied from the conducting electrode and a voltage value measured by the measuring electrode; and a state determining unit configured to determine a state of exercise on the basis of a first biometric impedance value of the user in a predetermined state and a second biometric impedance value of the user in a state of exercise different from the predetermined state.

* * * * *